US012766174B2

(12) United States Patent
Xiao et al.

(10) Patent No.: US 12,766,174 B2
(45) Date of Patent: Oct. 20, 2026

(54) *BIFIDOBACTERIUM ANIMALIS* **SUBSP. *LACTIS* ATM-209 INHIBITING HELICOBACTER PYLORI AND APPLICATION THEREOF**

(71) Applicant: SHENZHEN PORSHEALTH BIOENGINEERING CO., LTD., Shenzhen (CN)

(72) Inventors: Guoxun Xiao, Shenzhen (CN); Yanyi Zheng, Shenzhen (CN); Silu Zhang, Shenzhen (CN); Yuebiao Feng, Shenzhen (CN); Xin Teng, Shenzhen (CN)

(73) Assignee: SHENZHEN PORSHEALTH BIOENGINEERING CO., LTD., Shenzhen (CN)

( * ) Notice: Subject to any disclaimer, the term of this patent is extended or adjusted under 35 U.S.C. 154(b) by 264 days.

(21) Appl. No.: 18/604,772

(22) Filed: Mar. 14, 2024

(65) Prior Publication Data

US 2024/0390436 A1 Nov. 28, 2024

(30) Foreign Application Priority Data

May 22, 2023 (CN) ......................... 202310578935.7

(51) Int. Cl.
*A61K 35/745* (2015.01)
*A61P 31/04* (2006.01)
*C12N 1/205* (2026.01)

(52) U.S. Cl.
CPC ............ *A61K 35/745* (2013.01); *A61P 31/04* (2018.01); *C12N 1/205* (2021.05)

(58) Field of Classification Search
None
See application file for complete search history.

(56) References Cited

PUBLICATIONS

Jungersen et al (Microorganisms 2014, 2, 92-110; doi:10.3390/microorganisms2020092).*

* cited by examiner

*Primary Examiner* — Brian Gangle
(74) *Attorney, Agent, or Firm* — HOWARD M COHN and Associates, LLC

(57) ABSTRACT

The present invention relates to the technical field of microorganisms, in particular to a *Bifidobacterium animalis subsp. lactis* ATM-209 (GOLDGUT-BB18) inhibiting *Helicobacter Pylori* and an application thereof. The *Bifidobacterium animalis subsp. lactis* ATM-209 (GOLDGUT-BB18) provided by the present invention is preserved in China General Microbiological Culture Collection Center of China Committee for Culture Collection of Microorganisms, with a preservation number of CGMCC No. 25896. The strain has good acid tolerance, and can well adapt to a gastric environment; the strain has an obvious effect for inhibiting the growth of *Helicobacter Pylori*, can inhibit the in-vivo colonization of the *Helicobacter Pylori* in an animal experiment and relieve the inflammation caused by *Helicobacter Pylori* infection, and has broad application prospects in clinical prevention, treatment and inhibition of diseases related to *Helicobacter pylori* infection and gastrointestinal health food.

3 Claims, 8 Drawing Sheets

A B C D

*BIFIDOBACTERIUM ANIMALIS* SUBSP. *LACTIS* ATM-209 INHIBITING HELICOBACTER PYLORI AND APPLICATION THEREOF

TECHNICAL FIELD

The present invention relates to the technical field of microorganisms, in particular to a *Bifidobacterium animalis subsp. lactis* ATM-209 (GOLDGUT-BB18) inhibiting *Helicobacter Pylori* and an application thereof.

BACKGROUND

*Helicobacter Pylori* (Hp) is a helical, flagellated and micro-aerobic Gram-negative bacterium. *Helicobacter pylori* infection is one of the most common chronic bacterial diseases of the human beings. *Helicobacter pylori* is also a first-class human carcinogen recognized by the World Health Organization (WHO) and the International Agency for Research on Cancer (IARC). When *Helicobacter pylori* infects the stomach and is colonized, a lot of urease may be secreted to convert urea in gastric mucus into ammonia to neutralize gastric acid, so as to avoid being affected by the gastric acid, and then *Helicobacter Pylori* may proliferate greatly in the stomach and duodenum to destroy the gastric mucosal barrier, induce the cell apoptosis of the gastric mucosa, and lead to tissue damage and ulcer formation. Therefore, the *Helicobacter Pylori* infection is related to gastrointestinal malignant and non-malignant diseases, such as gastritis, chronic dyspepsia, mucosa-associated lymphoid tissue lymphoma, gastric adenocarcinoma, etc. The most common cause of gastric cancer is *Helicobacter Pylori* infection, so inhibiting the *Helicobacter Pylori* infection is a most effective method for preventing the gastric cancer.

Three or four different medicine or antibiotics may be usually used for treating the *Helicobacter Pylori* infection so as to achieve sufficient eradication rate. In recent years, due to the increasing drug resistance of more and more *Helicobacter Pylori* strains to the antibiotics, the effectiveness of numerous treatment solutions also decreases; and moreover, some antibiotics may cause more side effects and adverse effects. Therefore, relevant researchers in the art are committed to exploring an effective treatment method with no side effect, such as using probiotics combined with antibiotics to treat or eradicate the *Helicobacter Pylori* infection, wherein the probiotics can reduce the drug resistance of the antibiotics, and has an action of balancing intestinal flora and improving intestinal microecology.

Lactic acid bacteria (LAB) belong to a probiotic that is generally recognized as safe (GRAS) and is widely used in medicine, food and other industries. The lactic acid bacteria can ferment carbohydrates into lactic acid, which can be used for manufacturing yogurt, cheese, Chinese sauerkraut, beer, wine, pickles, pickled food and other fermented food. The common lactic acid bacteria include *Lactobacillus, Bifidobacterium, Lactococcus, Streptococcus, Pediococcus, Leuconostoc*, etc. The lactic acid bacteria can have numerous beneficial effects human hosts, including anti-allergic effects, antibacterial action, regulation of intestinal microbial flora, stimulation of immune system and prevention of colon cancer, and there are some researches on the application of the lactic acid bacteria strains in anti-*Helicobacter Pylori*.

In order to better meet the clinical practice requirements, it is necessary to develop diversified and effective probiotics to inhibit and treat diseases related to the *Helicobacter Pylori* infection.

SUMMARY

The present invention provides a *Bifidobacterium animalis subsp. lactis* ATM-209 (GOLDGUT-BB18) inhibiting *Helicobacter Pylori* and an application thereof.

The present invention provides a *Bifidobacterium animalis subsp. lactis* ATM-209 (GOLDGUT-BB18). The strain is preserved in China General Microbiological Culture Collection Center (abbreviated as CGMCC, address: Institute of Microbiology, China Academy of Sciences, No. 3, No. 1 Courtyard, Beichen West Road, Chaoyang District, Beijing, 100101), and classified and named *Bifidobacterium animalis subsp. lactis* with a preservation number CGMCC No. 25896.

The *Bifidobacterium animalis subsp. lactis* ATM-209 (GOLDGUT-BB18) was isolated from feces of healthy infants. The strain was identified by bacterial morphology, physiology and 16S rDNA (SEQ ID NO. 1) sequencing, and an identification result was *Bifidobacterium animalis subsp. lactis*, named *Bifidobacterium animalis subsp lactis* ATM-209 (GOLDGUT-BB18). The strain has good gastric acid tolerance, has an obvious effect for inhibiting the growth of *Helicobacter Pylori*, can significantly reduce the load of *Helicobacter Pylori* in the stomach and relieve the inflammation caused by pathogenic infection in animal experiments, and provides strain resources for developing food (such as dietary supplements, and health products), medicine and the like inhibiting the *Helicobacter Pylori*.

The *Bifidobacterium animalis subsp. lactis* ATM-209 (GOLDGUT-BB18) has the following microbiological traits:

(1) Morphological Features

Positive in gram stain, straight rod or curved short rod under a light microscope, in single or paired arrangement, V-shaped or curved shape; and colonies formed on an MRS solid culture medium are smooth, convex, entire-edged, milky white, glistening and soft in tissues.

(2) Physiological Traits

The *Bifidobacterium animalis subsp. lactis* ATM-209 (GOLDGUT-BB18) can grow well under an artificial gastric acid condition, and can inhibit the growth of *Helicobacter Pylori* in an in-vitro culture experiment with a diameter of a bacteriostatic ring reaching 18.0 mm, and can inhibit the in-viivo colonization of *Helicobacter Pylori* and relieve the inflammation caused by the pathogenic infection in animal experiments.

The *Bifidobacterium animalis* subsp. *lactis* ATM-209 (GOLDGUT-BB18) can be cultured by the following method: the *Bifidobacterium animalis* subsp. *lactis* ATM-209 (GOLDGUT-BB18) is inoculated to a culture medium and subjected to anaerobic culture at 35-37° C., wherein the culture time may be 12-24 h. The culture medium can adopt the conventional culture medium in the art capable of making the *Bifidobacterium animalis* subsp. *lactis* ATM-209 (GOLDGUT-BB18) grow, and preferably adopt an MRS meat soup culture medium (casease digesta 10.0 g/L, beef extract powder 10.0 g/L, yeast extract powder 4.0 g/L, triammonium citrate 2.0 g/L, sodium acetate 5.0 g/L, magnesium sulfate heptahydrate 0.2 g/L, manganese sulfate tetrahydrate 0.05 g/L, glucose 20.0 g/L, dipotassium phosphate 2.0 g/L, and polyoxyethylene sorbitan monooleate 1.0 g/L, pH=5.7±0.2), and the solid culture medium is added with 1.5% agar.

Through safety assessment, the acute oral toxicity test is carried out according to relevant provisions of GB 15193.3-2014, and results show that behaviors and metal status of mice are good, and the *Bifidobacterium animalis subsp. lactis* ATM-209 (GOLDGUT-BB18) belongs to an actual non-toxic level; according to relevant provisions of Food Strains Safety Evaluation Procedures (Draft for Comment) of Food Safety National Standard, after sequencing the whole genome of the *Bifidobacterium animalis subsp. lactis* ATM-209 (GOLDGUT-BB18), sequences of the whole genome are compared with sequences stored in latest versions of CARD, ResFinder, Argannot and NDARO, and in combination with an antibiotics drug resistance test experiment, the results prove that the strain does not contain a transferable antibiotics resistant gene; and the sequences of the whole genome are compared with latest sequences in VFDB, PAI, DB, MvirDB and CGE databases, and the results show that the strain does not contain any toxic factor.

The present invention provides a microbial preparation, and the microbial preparation includes *Bifidobacterium animalis subsp. lactis* ATM-209 (GOLDGUT-BB18).

Preferably, in the above microbial preparation, the *Bifidobacterium animalis subsp. lactis* ATM-209 (GOLDGUT-BB18) presents in a form of live bacteria.

The above microbial preparation may be a solid preparation (such as bacterial powder) or liquid preparation (such as emulsion preparations).

The present invention provides a method for preparing the above microbial preparation. The method includes a step of culturing the *Bifidobacterium animalis subsp. lactis* ATM-209 (GOLDGUT-BB18).

Preferably, the culture is anaerobic culture under a condition of 35-37° C.

Preferably, the culture is anaerobic culture in liquid culture medium to obtain a bacterial solution.

The bacterial solution may be directly made into the liquid preparation or may be made into the liquid preparation by concentration and/or by adding other ingredients, or may be dried to prepare solid preparations, or bacteria in the bacterial solution may be isolated for preparing the solid preparations.

Based on the function of the *Bifidobacterium animalis subsp. lactis* ATM-209 (GOLDGUT-BB18), the present invention provides following applications of the strain:

The present invention provides an application of the *Bifidobacterium animalis subsp. lactis* ATM-209 (GOLDGUT-BB18) or the microbial preparation in preparing a product inhibiting *Helicobacter Pylori.*

The present invention provides an application of the *Bifidobacterium animalis subsp. lactis* ATM-209 (GOLDGUT-BB18) or the microbial preparation in inhibiting *Helicobacter Pylori.*

Inhibiting the *Helicobacter Pylori* includes in-vitro inhibition of the growth of *Helicobacter Pylori*, or in vivo inhibition of colonization, infection, proliferation and growth of *Helicobacter Pylori.*

The present invention provides an application of the *Bifidobacterium animalis subsp. lactis* ATM-209 (GOLDGUT-BB18) or the microbial preparation in preparing a product for preventing, relieving or treating *Helicobacter Pylori* infection or diseases caused by the *Helicobacter Pylori* infection.

The diseases caused by the *Helicobacter Pylori* infection are preferably gastrointestinal diseases, including gastritis, gastric ulcer, duodenal ulcer, gastric cancer, and the like.

The present invention provides an application of the *Bifidobacterium animalis subsp. lactis* ATM-209 (GOLDGUT-BB18) or the microbial preparation in preparing a product for preventing, relieving or treating inflammation caused by *Helicobacter Pylori* infection.

The inflammation caused by the *Helicobacter Pylori* infection includes inflammation of gastric mucosa tissues, duodenal inflammation, etc.

The above products include food, feed, or medicine.

The present invention provides an application of the *Bifidobacterium animalis subsp. lactis* ATM-209 (GOLDGUT-BB18) or the microbial preparation in preparing food, feed or medicine.

In the present invention, the food includes ordinary food, dietary supplements and health products.

The present invention provides a food. The food includes *Bifidobacterium animalis subsp. lactis* ATM-209 (GOLDGUT-BB18) or the microbial preparation.

Besides the *Bifidobacterium animalis subsp. lactis* ATM-209 (GOLDGUT-BB18) or the microbial preparation, the food may also include raw materials allowed in the food field. The food may be a dietary supplement, a health product or fermented food.

The present invention provides medicine. The medicine includes *Bifidobacterium animalis subsp. lactis* ATM-209 (GOLDGUT-BB18) or the microbial preparation.

Besides the *Bifidobacterium animalis subsp. lactis* ATM-209 (GOLDGUT-BB18) or the microbial preparation, the medicine may also include ingredients in allowed the medicine field (such as filler, formant, lubricant, wetting agent, diluting agent, etc.) The preparation types of the medicine can be solid preparations (such as powder, granules, capsules, tablets, etc.) or liquid preparations (such as oral liquid, etc.).

The present invention at least has the following beneficial effects: the *Bifidobacterium animalis subsp. lactis* ATM-209 (GOLDGUT-BB18) provided by the present invention grows well in an environment with gastric acid, has good acid tolerance, and can well adapt to the gastric environment; and the strain has an obvious effect for inhibiting the growth of *Helicobacter Pylori*, can inhibit the in-vivo colonization of *Helicobacter Pylori* and reduce the load of *Helicobacter Pylori* in the animal experiments, and can relieve the inflammation caused by the *Helicobacter Pylori* infection, thereby playing a role in regulating the microbial flora of digestive tracts.

The *Bifidobacterium animalis subsp. lactis* ATM-209 (GOLDGUT-BB18) can be used for preparing the products for preventing, relieving or treating the *Helicobacter Pylori* infection or the diseases caused by the *Helicobacter Pylori* infection, and has broad application prospects in clinical prevention, treatment and inhibition of diseases related to *Helicobacter pylori* infection and gastrointestinal health food.

DESCRIPTION OF DRAWINGS

To more clearly describe the technical solutions in the present invention or in the prior art, the drawings required to be used in the description of the embodiments or in the prior art are simply presented below. Apparently, the following drawings show some embodiments of the present invention, so for those ordinary skilled in the art, other drawings can also be obtained according to these drawings without contributing creative labor.

DETAILED DESCRIPTION

Figure 1:
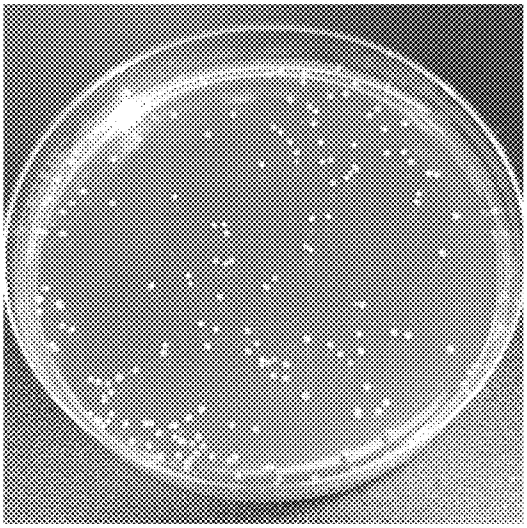
FIG. 1 is a diagram of colony morphology of *Bifidobacterium animalis subsp lactis* ATM-209 (GOLDGUT-BB18) on an MRS culture medium according to embodiment 1.

To make the purposes, technical solutions and advantages of the present invention clearer, the technical solutions in the present invention are described clearly and completely in conjunction with accompanying drawings in the present invention. Apparently, the described embodiments are some embodiments of the present invention, not all embodiments. All other embodiments obtained by a person of the ordinary skilled in the art based on the embodiments of the present invention without creative efforts shall fall within the protection scope of the present invention.

The strain of *Helicobacter Pylori* used in the following embodiments is *Helicobacter Pylori* NCTC11639, which is donated by Institute of Digestive Diseases in the First Affiliated Hospital of Nanchang University.

Embodiment 1 Isolation and Identification of *Bifidobacterium animalis subsp. lactis* ATM-209 (GOLDGUT-BB18

1. Isolation of *Bifidobacterium animalis subsp. lactis* ATM-209 (GOLDGUT-BB18)

1.1 Source of Samples

The strain of the *Bifidobacterium animalis subsp. lactis* used in the present invention was isolated from feces of healthy infants.

1.2 Preparation of a Culture Medium

An MRS culture medium was used for isolating samples and screening the strain, and the MRS culture medium included the following components: casease digesta 10.0 g/L, beef extract powder 10.0 g/L, yeast extract powder 4.0 g/L, triammonium citrate 2.0 g/L, sodium acetate 5.0 g/L, magnesium sulfate heptahydrate 0.2 g/L, manganese sulfate tetrahydrate 0.05 g/L, glucose 20.0 g/L, dipotassium phosphate 2.0 g/L, and polyoxyethylene sorbitan monooleate 1.0 g/L, the pH was 5.7±0.2, and 1.5% agar was added to form the MRS solid culture medium.

1.3 Isolation of the Strain 1 g of feces sample was placed into 10 mL of MRS liquid culture medium prepared in step 1.2, and uniformly mixed for culture at 36° C., 1 mL of enriched liquid was absorbed in a super clean bench to perform 10-times gradient dilution, 100 μL of bacterial solution at three dilution gradients, i.e. $10^{-5}$, $10^{-6}$ and $10^{-7}$ were selected and coated on a culture dish containing sterile MRS solid culture medium and stood and cultured for 24-48 h at 36° C. under an aerobic condition, until there were obvious single bacterial colonies formed, a plate grown with 70-120 single colonies was selected from the culture medium, typical colonies were selected and subjected to scribing purification multiple times on the MRS solid plate culture medium, and the culture with the same colony morphology on the whole plate was subjected to strain identification.

2. Identification of *Bifidobacterium animalis subsp. lactis* ATM-209 (GOLDGUT-BB18)

2.1 Features of Colonies

After the *Bifidobacterium animalis subsp. lactis* ATM-209 (GOLDGUT-BB18) was cultured for 24 h in the MRS solid culture medium, the colonies were smooth, convex, complete in edges, milky white, glistening and soft in texture, as shown in FIG. 1.

2.2 Morphology Under a Microscope

Figure 2:
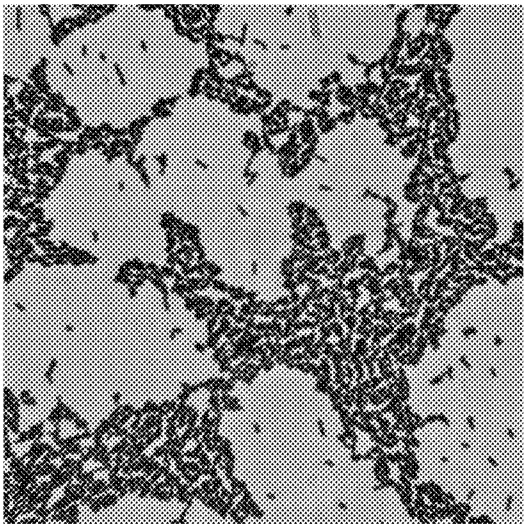
FIG. 2 is a microscopogram of *Bifidobacterium animalis subsp. lactis* ATM-209 (GOLDGUT-BB18) according to embodiment 1.

Colony smears of the *Bifidobacterium animalis subsp. lactis* ATM-209 (GOLDGUT-BB18): positive in gram staining, straight-rod or curved short rod under a light microscope, single or paired arrangement, V-shaped or curved shape, as shown in FIG. 2.

2.3 16S rDNA Identification

Identification unit: Tsingke Biotech Co., Ltd.

Identification sequence: The sequence of 16S rDNA is as shown by SEQ ID No. 1.

Identification result: according to a sequence contrast result and physiological and biochemical results of the strain, the strain was determined to be *Bifidobacterium animalis subsp. lactis.*

Embodiment 2 Detection of Gastric Acid Tolerance of *Bifidobacterium animalis subsp. lactis* ATM-209 (GOLDGUT-BB18

The overall pH condition in a gastric environment of the human body is strongly acidic, so that the acid tolerance of the strain is an important index for evaluating whether the strain can survive and colonize in the gastric acid environment. Artificial gastric fluid was used for simulating the gastric environment; in a gastric acid digestion group, 100 mL of artificial gastric fluid was added into a 96-pore plate containing 100 μL of bacterial solution of *Bifidobacterium animalis subsp. lactis* ATM-209 (GOLDGUT-BB18), and the mixture was mixed uniformly by blowing, and subjected to anaerobic co-incubation for 2 h at 37° C.; and in a control group, 100 μL of PBS was added into the 96-pore plate containing 100 μL of bacterial solution of *Bifidobacterium animalis subsp. lactis* ATM-209 (GOLDGUT-BB18), and the mixture was uniformly mixed by blowing, and subjected to anaerobic co-incubation for 2 h at 37° C., and after the incubation, the pore plate was taken out.

An incubation sample in the gastric acid digestion group was diluted with PBS to 10E-5; and the incubation sample in the control group was diluted with PBS to 10E-6. The diluted sample was coated on an MRS agar plate and subjected to anaerobic culture for 16 h at 37° C., then colony counting was carried out, a survival rate of the bacteria was calculated with a calculation formula as follows: survival rate/%=(variable count in the gastric acid digestion group log CFU/mL/variable count in the control group log CFU/mL)*100%.

Figure 3:
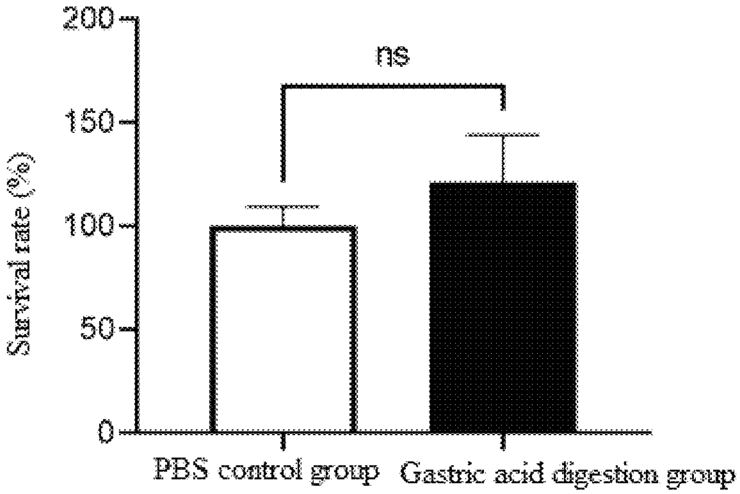
FIG. 3 shows comparison of a survival rate of *Bifidobacterium animalis subsp lactis* ATM-209 (GOLDGUT-BB18) after growing for 2 hours under artificial gastric acid and PBS control conditions according to embodiment 2, wherein data comes from three repeated experiments, an error line indicates a standard deviation, and ns indicates that there is no significant difference.

After being digested for 2 h in gastric acid, the survival rate of the *Bifidobacterium animalis subsp. lactis* ATM-209 (GOLDGUT-BB18) was 121% (as shown in FIG. 3), and there was no significant difference compared with the PBS control group, which showed that the strain was strong in acid tolerance, and could survive and colonize in the gastric environment.

Embodiment 3 In-Vitro Bacteriostatic Activity Test of *Bifidobacterium animalis subsp. lactis* ATM-209 (GOLDGUT-BB18

1. Strain Culture

*Helicobacter Pylori* NCTC11639 (abbreviated as *H. pylori*) was resuscitated by a blood plate culture medium, then inoculated to a BD liquid culture medium, and cultured for 48 h under a microaerophilic condition at 37° C.; and the *Bifidobacterium animalis subsp. lactis* ATM-209 (GOLDGUT-BB18) was activated by the MRS solid culture medium and inoculated to the MRS liquid culture medium to be cultured for 24 h at 37° C.

The microaerophilic condition refers to an environment with an oxygen concentration of 5% (percentage by volume), and a carbon dioxide concentration of 10% (percentage by volume).

2. Bacteriostasis Test

Figure 4:
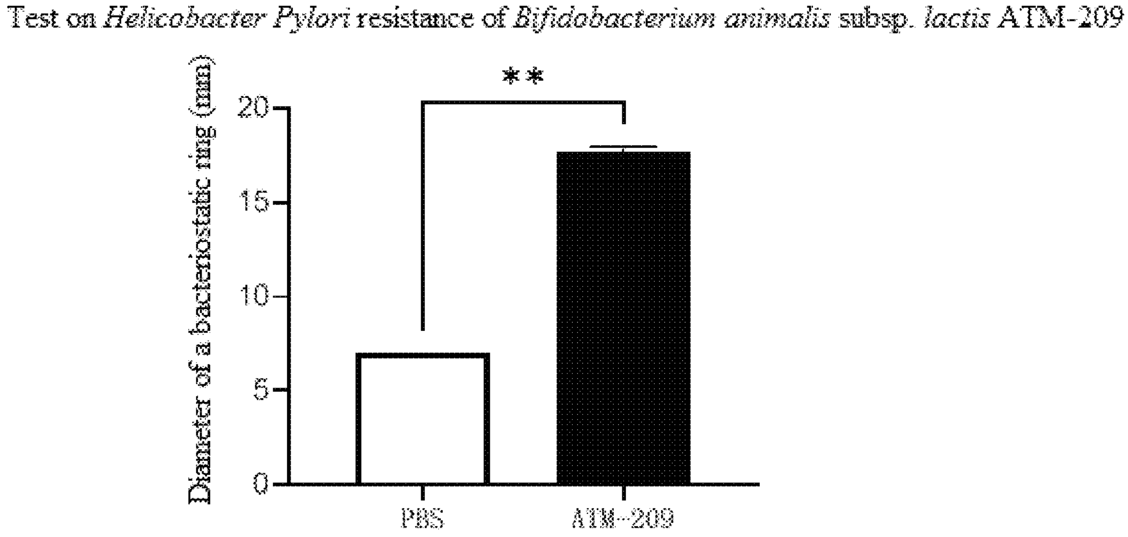
FIG. 4 shows a diameter of an in-vitro bacteriostatic ring of *Bifidobacterium animalis subsp. lactis* ATM-209 (GOLDGUT-BB18) according to embodiment 3, wherein data comes from two repeated experiments, and the error line indicates the standard deviation; and a statistics method is Student's t-test, and ** indicates that a value of p is less than 0.01.

Bacteriostasis test was carried out by a punching method, an overnight cultured bacterial solution of *Bifidobacterium animalis subsp. lactis* ATM-209 (GOLDGUT-BB18) was centrifuged at 6000 rpm for 10 min, and then supernatant was collected and sterilized by a 0.22 μm filter head to obtain strain fermentation supernatant. The *Helicobacter Pylori* was coated on an MH solid culture medium to 10E9 CFU, the plate was punched by a puncher after being dried, the strain fermentation supernatant was added into pores, and PBS was used as a negative control. The blood plate was cultured for 48 h in a microaerophilic incubator at 37° C., and a diameter of a bacteriostatic ring was measured. Compared with the PBS control group, the fermentation supernatant of the *Bifidobacterium animalis subsp. lactis* ATM-209 (GOLDGUT-BB18) significantly increased the diameter of the bacteriostatic ring (as shown in FIG. 4), which showed an obvious effect for in vitrio inhibiting the *Helicobacter Pylori.*

Embodiment 4 Test on Effect of *Bifidobacterium animalis subsp. lactis* ATM-209 (GOLDGUT-BB18) for Inhibiting *Helicobacter Pylori* in Gerbil Models Grouping: 36 Mongolian male gerbils at the age of 6-8 weeks were adaptively fed for one week and then randomly divided into 4 groups, i.e. a blank group (6 gerbils), Hp infection group (intragastric injection with *H. pylori,* 12 gerbils), an antibiotic drug group (first intragastric injection with *H. pylori*, and then intragastric injection with bismuth-containing quadruple, 6 gerbils), and a probiotic group (first intragastric injection with *H. pylori*, and then intragastric injection with *Bifidobacterium animalis subsp. lactis* ATM-209 (GOLDGUT-BB18), 12 gerbils).

Modeling: after the gerbils for modeling were subjected to fasting and refraining from water for 24 h, intragastric injection with 108 CFU of bacterial solution of *Helicobacter Pylori* was carried out by using a mouse gavage needle, and the intragastric injection lasted for 10 days.

Intervention: after confirming the success of modeling, the gerbil model was fed with antibiotic drugs and probiotics. The gerbils in the antibiotic drug group were treated with bismuth quadruple; the gerbils in the probiotic group were subjected to intragastric injection with 108 CFU of probiotics by using the mouse gavage needle, lasting for 21 days. The probiotics selected the bacterial solution with vigorous growth at logarithmic phase of growth. The gerbils in the Hp infection group and the gerbils in the blank group were also subjected to intragastric injection with normal saline by using a mouse gavage needle, lasting for 21 days.

Figure 5:
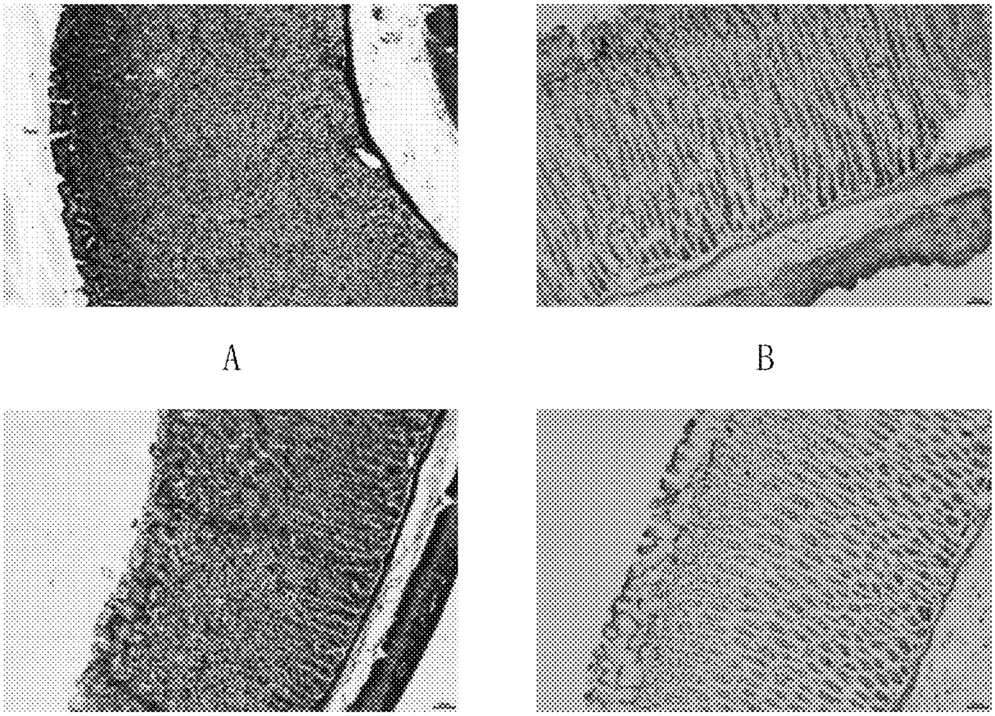
FIG. 5 shows result diagrams of silver nitrate staining of gastric tissues in different groups according to embodiment 4, wherein A: a blank group, B: an Hp infection group, C: an antibiotic drug group, and D: a probiotic group.

After 21-day intervention, the mice were killed to take gastric tissues which were fixed by 10% formalin, and then the fixed gastric tissues were sectioned by paraffin for warthin-Starry silver nitrate staining. Mucins on surfaces of spirochetes may be specifically bond with silver to be in black. In the silver nitrate staining diagram of gastric tissues in the Hp infection group, black short rod-like particles and hyphae can be seen, the stained degree is most serious, and the stained area is the largest. The antibiotic treatment can change the infection situation, and the *Bifidobacterium animalis subsp. lactis* ATM-209 (GOLDGUT-BB18) can slightly improve the infection situation (as shown in FIG. 5).

Embodiment 5 Pathological Analysis on Gastric Tissues in Gerbil Models

Figure 6:
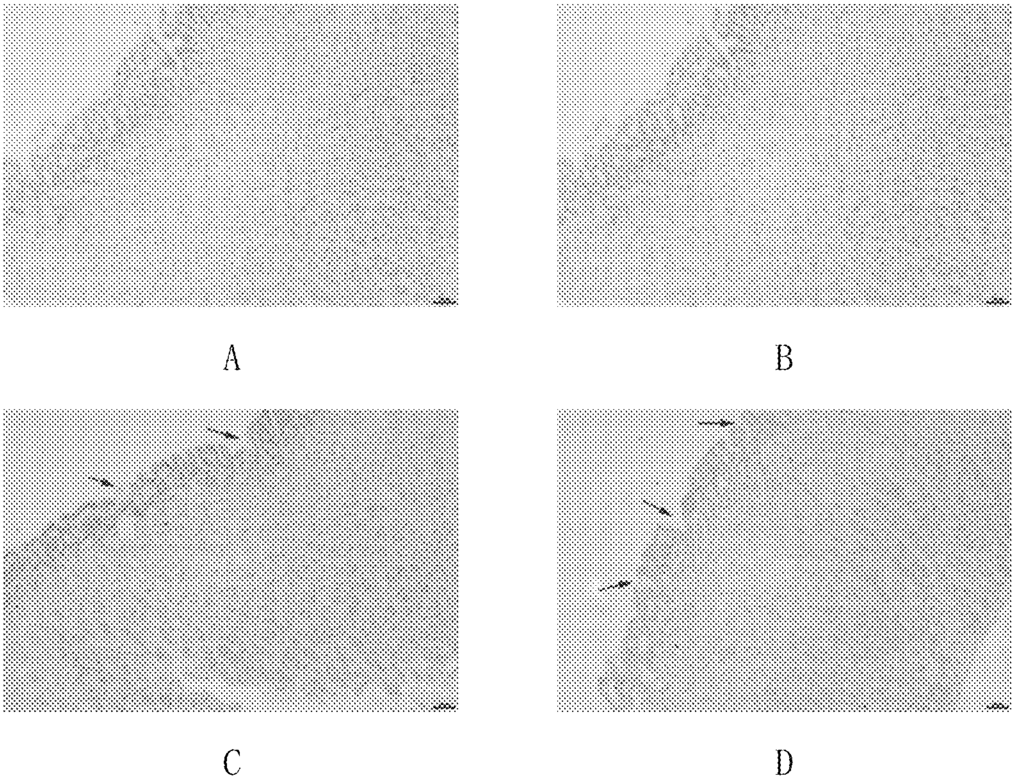
FIG. 6 shows result diagrams of hematoxylin-eosin staining of gastric tissues in different groups according to embodiment 5, wherein A: a blank group, B: an Hp infection group, C: an antibiotic drug group, and D: a probiotic group.

Gastric tissue sections of four groups of experimental gerbils after gastric injection in embodiment 4 were collected for hematoxylin-eosin staining. Results are shown in FIG. 6. The pictures all show the anterior stomach and the posterior stomach; and the anterior stomach is mainly squamous epithelium and the posterior stomach is columnar epithelium. The gastric wall mainly includes a mucosal layer, a submucous layer, a muscular layer and a serosal layer, and the tissue structure of each layer is normal. In the blank group, there was no degeneration and necrosis of mucosal epithelial cells, and no infiltration of inflammatory cells in the lamina propria and submucous layer; in the Hp infection group, mucosal epithelial cells were slightly degenerated and necrotic, and the lamina propria and submucous layer were rarely infiltrated with the inflammatory cells; and in the antibiotic drug group and probiotic group, the mucosal epithelial cells were slightly degenerated and necrotic, and the lamina propria and submucous layer were slightly infiltrated with the inflammatory cells. Scores of pathological tissues are shown in table 1. The above results show that like the antibiotics, the intervention with *Bifidobacterium animalis subsp. lactis* ATM-209 (GOLDGUT-BB18) relieves the gastric lesion and inflammation caused by the *Helicobacter Pylori* infection.

TABLE 1

Scores of pathological gastric tissues in different groups in embodiment 5

| | Histopathological examination record sheet | |
|---|---|---|
| Group | No. | Histopathological score |
| Blank group | 1 | 0 |
| | 2 | 0 |
| | 3 | 1 |
| | 4 | 0 |
| | 5 | 0 |
| Probiotic group | 1 | 1 |
| | 2 | 2 |
| | 3 | 1 |
| | 4 | 0 |
| | 5 | 1 |
| Antibiotic group | 1 | 1 |
| | 2 | 1 |
| | 3 | 0 |
| | 4 | 0 |
| | 5 | 1 |
| Infection group | 1 | 2 |
| | 2 | 1 |
| | 3 | 2 |
| | 4 | 2 |
| | 5 | 2 |

Note:
according to the change degree, all morphological changes are marked as a score such as "1", "2", "3" and "4", indicating slight, mild, moderate and severe respectively, no pathological change is marked as "0", and absence is marked as "none".

Embodiment 6 Urease Analysis on Gastric Mucosa Tissues in Gerbil Models

Figure 7:
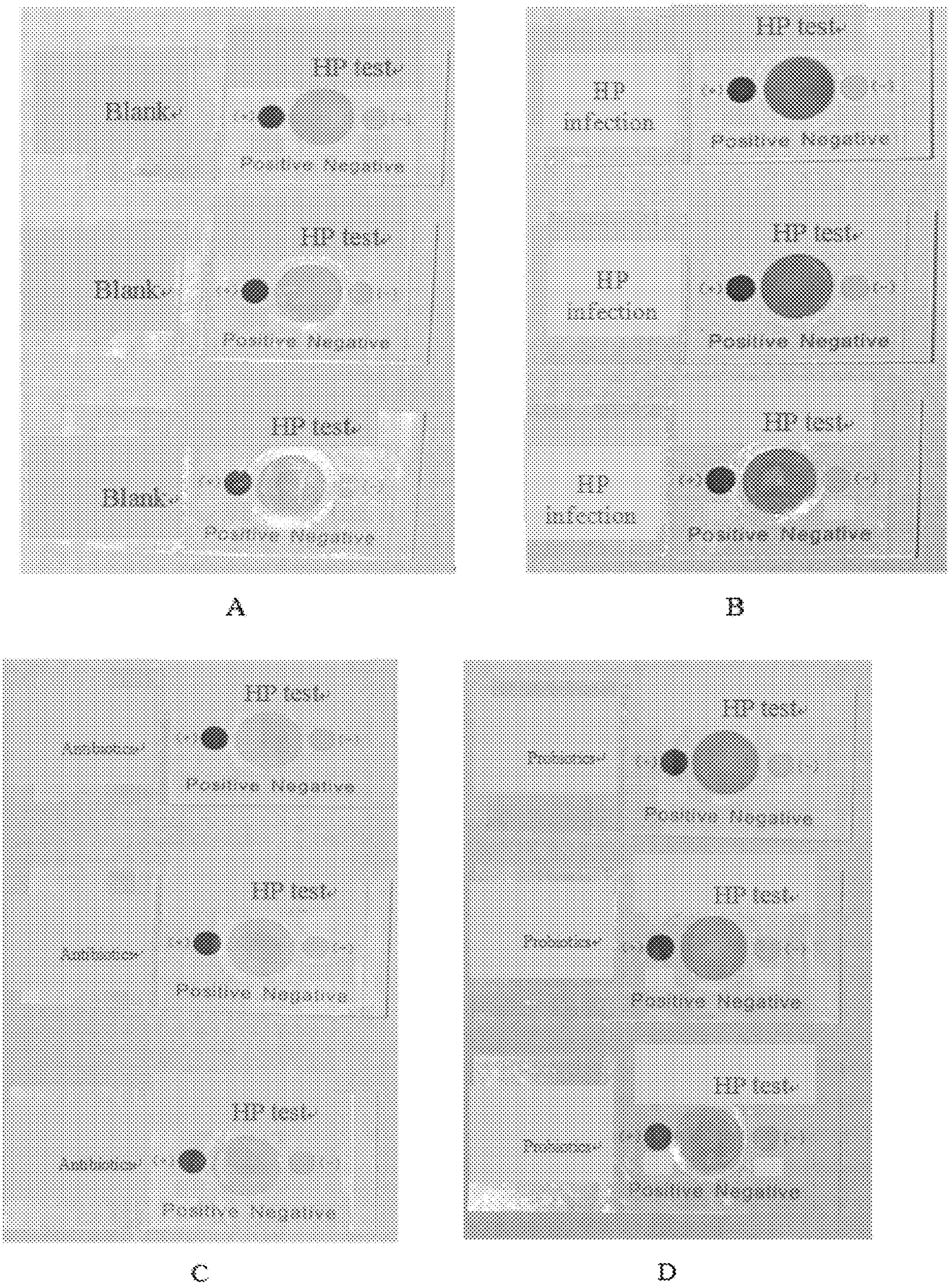
FIG. 7 shows result diagrams of urease detection of gastric mucosa tissues in different groups according to embodiment 6, wherein A: a blank group, B: an Hp infection group, C: an antibiotic drug group, and D: a probiotic group.

Hp may generate a large number of urease in the stomach, so that the Hp infection may be judged by detecting the urease. The final color of urease yellow test paper is regarded as negative, and regarded as positive if the final color is rose or light red. The gastric mucosa tissues of four groups of experimental gerbils after gastric injection in embodiment 4 were taken with a toothpick, and were placed on the center of the urease yellow test paper, then a self-adhesive sticker was laminated to a plastic film, so that the self-adhesive sticker was tightly combined with the plastic film, and 1-3 min later, the color change of the test paper was observed, as shown in FIG. 7. In the antibiotic drug group and the blank group, Hp was not shown in positive, while the Hp results in the Hp infection group and the probiotic group were positive; however, compared with the infection group, the color of the test paper of the probiotic group was obviously yellow, which showed that the intervention with *Bifidobacterium animalis subsp. lactis* ATM-209 (GOLDGUT-BB18) can obviously reduce the load of *Helicobacter Pylori*.

Figure 8:
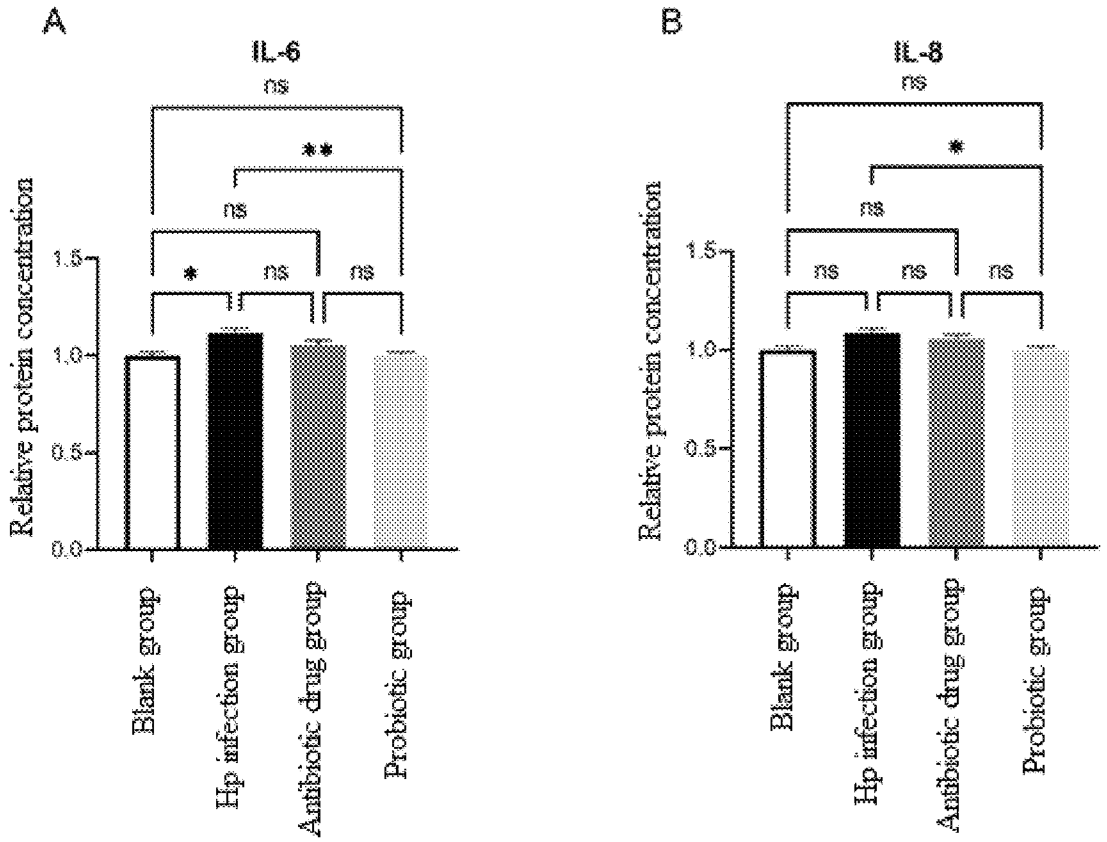
FIG. 8 shows diagrams of determination results of content of proinflammatory cytokine interleukin-6 (IL-6, A) and proinflammatory cytokine interleukin-8 (IL-8, B) of gastric mucosa tissues in different groups according to embodiment 7, wherein a relative protein concentration is a relative value of each group of protein concentration after normalization relative to the protein concentration of the blank group; an error line indicates a standard deviation; a statistical analysis method is One-Way ANOVA, * indicates that a value of p is less than 0.05, ** indicates that the value of p is less than 0.01, and ns indicates that there is no significant difference.

Embodiment 7 Analysis on Inflammation of Gastric Mucosa Tissues in Gerbil Models The gastric mucosa tissues of four groups of experimental gerbils after intragastric injection in embodiment 4 were collected, added with RIPA lysate and fully homogenized, and then proteins were extracted from the tissues. The total protein content was determined by a BCA kit. The contents of proinflammatory cytokine-6 (IL-6) and proinflammatory cytokine-8 (IL-8) were determined by an enzyme-linked immunosorbent assay kit. It can be seen from FIG. 8 that compared with the infection group, the probiotic treatment significantly reduces the protein levels of IL-6 and IL-8, and the protein levels of IL-6 and IL-8 in the probiotic group are significantly lower than the antibiotic drug group, which shows that the *Bifidobacterium animalis subsp. lactis* ATM-209 (GOLDGUT-BB18) can relieve the inflammatory reaction of the gastric tissues caused by the *Helicobacter Pylori* infection, and the effect is better than the conventional antibiotics for treating the *Helicobacter Pylori* infection.

In conclusion, the present invention obtains *Bifidobacterium* animalis *subsp. lactis* through isolation and screening, which is named as *Bifidobacterium* animalis *subsp. lactis* ATM-209 (GOLDGUT-BB18). The experiments for in-vitro acid tolerance and growth inhibition of *Helicobacter Pylori* of the *Bifidobacterium animalis subsp. lactis* prove that the *Bifidobacterium animalis subsp. lactis* has strong acid tolerance to the gastric environment, and has an effect for inhibiting the growth of *Helicobacter Pylori*. It is further discovered that the *Bifidobacterium animalis subsp. lactis* can effectively reduce the in vivo growth of *Helicobacter Pylori* and relieve the gastric tissue inflammation caused by the *Helicobacter Pylori* infection through the Mongolian gerbil models. Therefore, the strain is suitable for the digestive tract environment, has excellent capacity for resisting the *Helicobacter Pylori*, and has broad application prospect in the aspect of resisting the gastrointestinal pathogen *Helicobacter Pylori*.

Finally, it should be noted that the above embodiments are only used for illustrating the technical solutions of the present invention rather than limiting the present invention. Although the present invention is described in detail with reference to the above embodiments, it should be understood by those skilled in the art that the technical solutions described in the above embodiments may be modified or some technical features may be equivalently substituted. However, these modifications or substitutions do not make the essence of the corresponding technical solutions depart from the spirit and scope of the technical solutions of various embodiments of the present invention.

What is claimed is:

1. A method for preparing a microbial product, comprising:

culturing a *Bifidobacterium animalis* subsp. *lactis* ATM-209 and obtaining a bacterial solution; wherein, the *Bifidobacterium animalis* subsp. *lactis* ATM-209 is preserved in China General Microbiological Culture Collection Center of China Committee for Culture Collection of Microorganisms, with a preservation number of CGMCC No. 25896;

preparing the bacterial solution into a liquid microbial preparation directly or by concentration and/or addition of other excipients, or into a solid preparation by drying, or separating *Bifidobacterium animalis* subsp. *lactis* ATM-209 in the bacterial solution and preparing the bacteria into a solid preparation.

2. The method according to claim 1, wherein the culture is anaerobic culture under a condition of 35-37° C.

3. A method for treating *Helicobacter Pylori* infection, comprising:

administrating a microbial product for inhibiting *Helicobacter Pylori* into a body;

wherein, the administered microbial product comprises a *Bifidobacterium animalis* subsp. *lactis* ATM-209 that is preserved in China General Microbiological Culture Collection Center of China Committee for Culture Collection of Microorganisms, with a preservation number of CGMCC No. 25896.

* * * * *